United States Patent
Baid

(10) Patent No.: US 10,368,790 B2
(45) Date of Patent: Aug. 6, 2019

(54) NEEDLE SAFETY ASSEMBLY

(71) Applicant: Poly Medicure Limited, Kolkata (IN)

(72) Inventor: Rishi Baid, New Delhi (IN)

(73) Assignee: POLY MEDICURE LIMITED, Faridabad (IN)

( * ) Notice: Subject to any disclaimer, the term of this patent is extended or adjusted under 35 U.S.C. 154(b) by 193 days.

(21) Appl. No.: 14/431,433

(22) PCT Filed: Oct. 21, 2013

(86) PCT No.: PCT/IB2013/059510
§ 371 (c)(1),
(2) Date: Mar. 26, 2015

(87) PCT Pub. No.: WO2014/064599
PCT Pub. Date: May 1, 2014

(65) Prior Publication Data
US 2015/0257693 A1    Sep. 17, 2015

(30) Foreign Application Priority Data

Oct. 23, 2012    (IN) .......................... 1225/KOL/2012

(51) Int. Cl.
*A61M 5/00*        (2006.01)
*A61B 5/15*        (2006.01)
(Continued)

(52) U.S. Cl.
CPC ....... *A61B 5/150641* (2013.01); *A61M 5/158* (2013.01); *A61M 5/3271* (2013.01);
(Continued)

(58) Field of Classification Search
CPC .. A61M 2005/1586; A61M 2005/3247; A61M 25/0631; A61M 25/0637;
(Continued)

(56) References Cited

U.S. PATENT DOCUMENTS 5,772,638 A    6/1998  Utterberg et al.
2004/0153039 A1    8/2004  Wang
(Continued)

FOREIGN PATENT DOCUMENTS

EP    2 055 344 A1    5/2009
WO    03105928 A1    12/2003
(Continued)

OTHER PUBLICATIONS

PCT International Search Report; International Application No. PCT/IB2013/059510; Applicant: Poly Medicure Limited; Date of Actual Completion of Interational Search: May 22, 2014; dated May 30, 2014.

*Primary Examiner* — Rebecca E Eisenberg
(74) *Attorney, Agent, or Firm* — Bodi Law LLC

(57) ABSTRACT

A needle safety assembly comprising a needle and a protective cover for the needle, wherein the needle is attached to a needle hub having wings on opposite sides which can be moved relative to the protective cover from a position of use where the tip of the needle is outside of the protective cover into a retracted position in which the needle is fully received in the protective cover. The protective cover is of generally tubular shape having two opposite axial slots extending from a distal end of the protective cover towards a tubular base portion of the protective cover. The slots are adapted to receive the wings when the needle hub moves into the protective cover. Also provided is a locking mechanism adapted to secure the needle hub inside the protective cover when the needle hub is retracted.

14 Claims, 7 Drawing Sheets

Figure 1A:
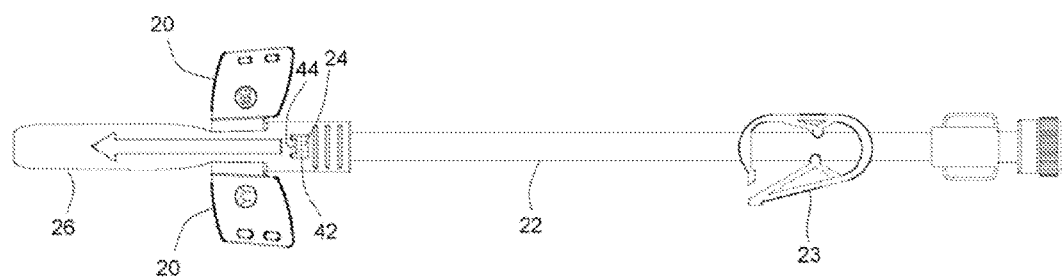

(51) Int. Cl.
*A61M 5/32* (2006.01)
*A61M 25/06* (2006.01)
*A61M 5/158* (2006.01)

(52) U.S. Cl.
CPC .... *A61M 25/0631* (2013.01); *A61M 25/0637* (2013.01); *A61M 2005/1586* (2013.01); *A61M 2005/3247* (2013.01)

(58) Field of Classification Search
CPC .. A61M 5/158; A61M 5/3271; A61M 5/3243; A61B 5/150641
See application file for complete search history.

(56) References Cited

U.S. PATENT DOCUMENTS

| | | | |
|---|---|---|---|
| 2006/0100575 A1* | 5/2006 | Restelli | A61M 25/0637 604/110 |
| 2007/0118082 A1 | 5/2007 | Mori | |
| 2008/0082052 A1 | 4/2008 | Schnell et al. | |
| 2011/0301552 A1 | 12/2011 | Nakanishi et al. | |

FOREIGN PATENT DOCUMENTS

| | | |
|---|---|---|
| WO | 2010038844 A1 | 4/2010 |
| WO | 2012009599 A1 | 1/2012 |

\* cited by examiner

NEEDLE SAFETY ASSEMBLY

CROSS-REFERENCES TO RELATED APPLICATIONS

This application is the national phase of International Application No. PCT/IB2013/059510 filed on Oct. 21, 2013, which claims priority from Indian Patent Application No. 1225/KOL/2012 dated Oct. 23, 2012, the entire disclosures of which are incorporated herein by reference.

FIELD OF THE INVENTION

The present invention relates to a needle safety assembly, in particular for a disposable medical device, comprising a needle and a protective cover for the needle, wherein the needle is attached to a needle hub which can be moved relative to the protective cover between a position of use in which at least the tip of the needle is outside of the protective cover, and a retracted position in which the needle is fully received in the protective cover.

BACKGROUND OF THE INVENTION

Healthcare workers are increasingly at risk of disease transmission, and nurses perform the majority of invasive hypodermic procedures, such as injecting medicine, collecting blood and inserting indwelling intravenous (I.V.) catheters. Nurses and other healthcare personnel are routinely injured by the exposed, sharp lancet of the needle after use on a patient. The critical time where a percutaneous injury can occur is from the moment the needle is withdrawn from the patient, or I.V. port, to the time the contaminated needle is safely discarded.

Prior to the proliferation of HIV and serum hepatitis, a needle stick injury was considered a routine part of providing patient care. A needle stick injury now carries a life-threatening consequence and healthcare workers must live with this terror on a daily basis. Hence, there is a requirement for a low-cost safety needle protector apparatus with a universal application which shall prevent accidental contact of a medical professional or any other person with the sharp tip of the needle after use of the disposable medical device and thus prevent possible transmission of an infectious disease such as hepatitis, HIV, etc.

It is an object of the present invention to provide a needle safety assembly which provides reliable protection against accidental pricking by a hypodermic needle and which is easy and inexpensive to manufacture.

This object is satisfied by a needle safety assembly comprising a needle and a protective cover for the needle, wherein the needle is attached to a needle hub which has wings provided on opposite sides of the needle hub and which can be moved relative to the protective cover from a position of use in which at least the tip of the needle is outside of the protective cover into a retracted position in which the needle is fully received in the protective cover, wherein the protective cover is of generally tubular shape and defines two opposite axial slots which extend from a distal end of the protective cover towards a tubular base portion of the protective cover, wherein the slots are adapted to receive the wings when the needle hub moves into the protective cover, and wherein the needle safety assembly further comprises a locking mechanism adapted to secure the needle hub inside the protective cover when the needle hub is in the retracted position.

SUMMARY OF THE INVENTION

A needle safety assembly of the invention comprises a needle and a protective cover for the needle, wherein the needle is attached to a needle hub which has wings provided on opposite sides of the needle hub and which can be moved relative to the protective cover from a position of use in which at least the tip of the needle is outside of the protective cover into a retracted position in which the needle is fully received in the protective cover. The protective cover is of generally tubular shape and defines two opposite axial slots which extend from a distal end of the protective cover towards a tubular base portion of the protective cover, wherein the axial slots are adapted to receive the wings when the needle hub moves into the protective cover, and wherein the needle safety assembly further comprises a locking mechanism adapted to secure the needle hub inside the protective cover when the needle hub is in the retracted position.

In other words, the invention proposes a needle safety assembly which locks the needle safely in the protective cover by an interlocking arrangement. The locking mechanism effectively prevents the needle from inadvertently protruding out of the protective cover. Thereby protection against accidental pricking by the needle is greatly increased. Consequently, the needle safety assembly of the invention ensures a safe disposal of the needle after its use.

It is to be noted that in the context of this invention the term 'needle' comprises any object having a sharp tip which can cause a percutaneous injury. Specifically, in this context the term 'needle' is understood to not only refer to a needle in the literal sense but also to a blade which has a sharp tip.

Disposable medical devices in which the needle safety assembly can be used include, for example, devices which are used to collect blood from a patient or a donor or to give fluids to a patient, such as blood collection sets (e.g. PSV sets with Luer adapters), blood collection bag needles, scalp vein sets, and fistula needles.

According to a preferred embodiment, the locking mechanism comprises at least one pair of first and second locking means engaging with each other when the needle hub is in the retracted position, wherein the first locking means is provided on the needle hub and the second locking means is provided on the protective cover.

In the case of more than one pair of first and second locking means, at least one pair of first and second locking means may be arranged on a first side of the needle safety assembly, while at least another pair of first and second locking means may be arranged on a second side of the needle safety assembly opposite from the first side, when the needle hub is in the retracted position. Alternatively, it is also possible to have only one first locking means and more than one second locking means, e.g. two opposite second locking means, or vice versa.

The needle safety assembly is particularly inexpensive to manufacture, if the first locking means is formed integrally with the needle hub and/or the second locking means is formed integrally with the protective cover.

Preferably, the first locking means defines a surface facing the needle tip, wherein at least a portion of the surface extends in a plane generally perpendicular to the needle. This makes a particularly effective interaction between the first and second locking means possible.

According to a preferred embodiment, the first locking means comprises a protrusion protruding from the needle hub.

For example, the first locking means may have a generally nose-like or ramp-like shape, with its radial dimension increasing towards the tip of the needle.

In order to facilitate the movement of the needle hub into an interior passage of the protective cover, the first locking means may be formed such that a radial dimension of the locking means can be reduced against a restoring force. For example, the first locking means may comprise a material having elastic properties.

The first locking means may be arranged in the region of a proximal end of the needle hub. This arrangement is particularly advantageous in the case of winged needle hub.

According to a further embodiment, the second locking means is provided on the tubular base portion of the protective cover.

The second locking means may comprise an opening in the protective cover, which is adapted to receive the first locking means, e.g. a protrusion protruding from the needle huh, when the needle hub is in the retracted position, thereby interlocking the needle hub and the protective cover.

Additionally or alternatively, the second locking means may comprise a locking tongue extending towards a proximal end of the protective cover and adapted to engage with the first locking means, when the needle hub is in the retracted position.

Preferably, the locking tongue extends towards the interior of the protective cover. It may have resilient properties such that it can be pushed outwards by the first locking means as the needle hub is moved towards its retracted position, and snap back behind the first locking means once the needle hub has adopted its retracted position. This is particularly advantageous if the first locking means does not have elastic properties. Alternatively, the locking tongue may be rigid if the first locking means comprises an elastic material.

BRIEF DESCRIPTION OF THE ACCOMPANYING DRAWINGS

Figure 1B:
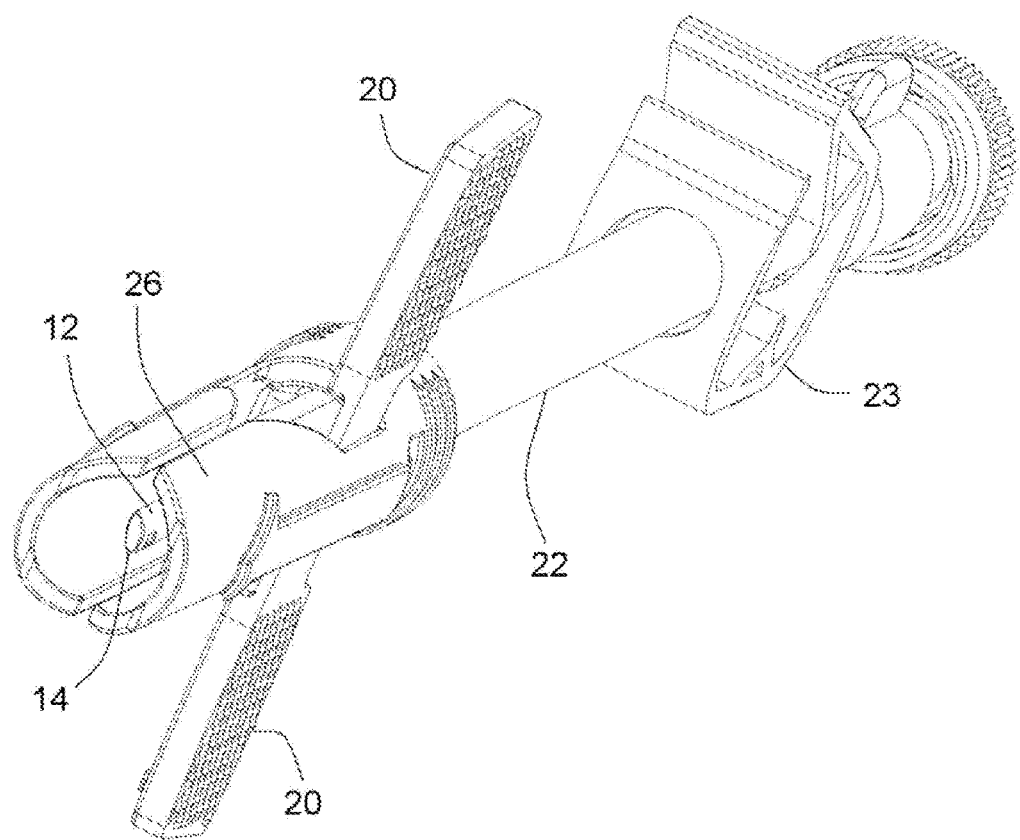
Figure 1C:
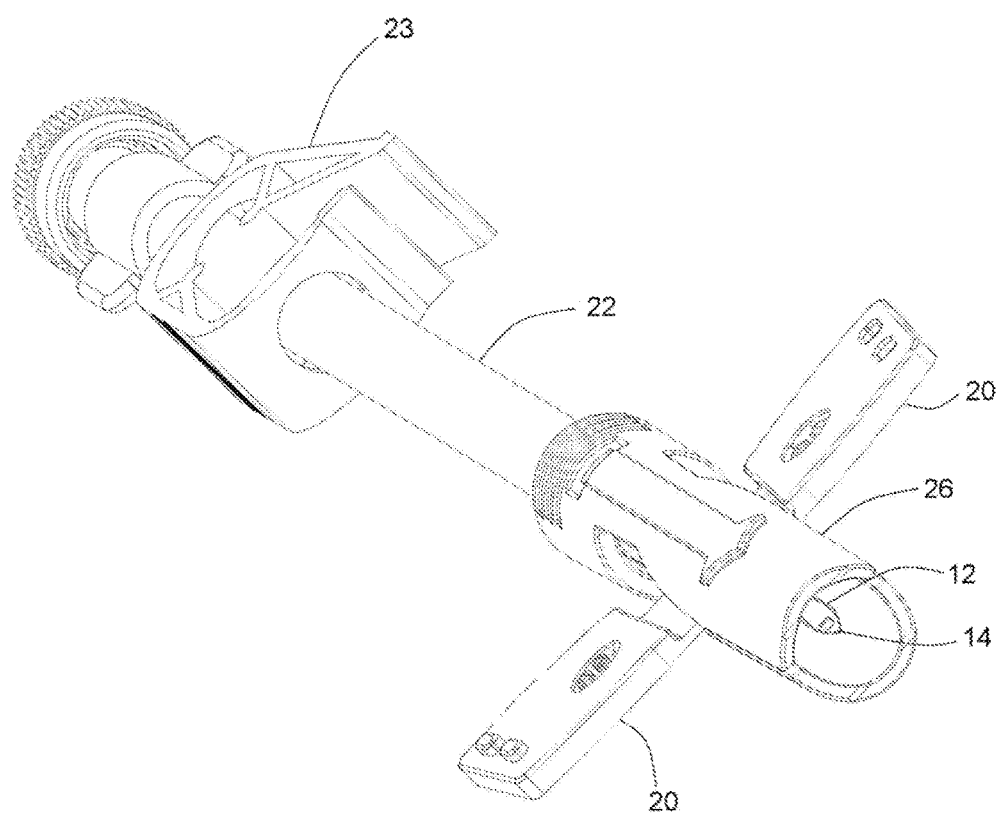
Figure 2A:
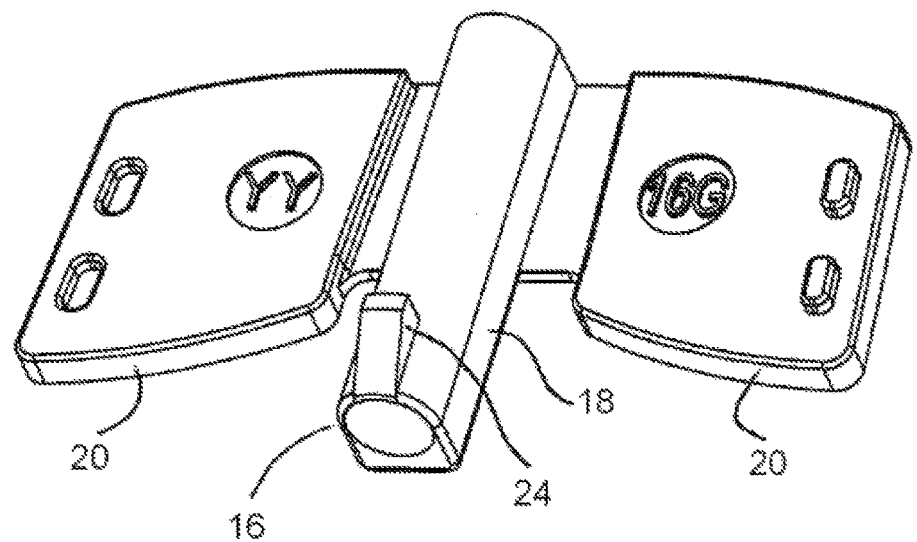
Figure 2B:
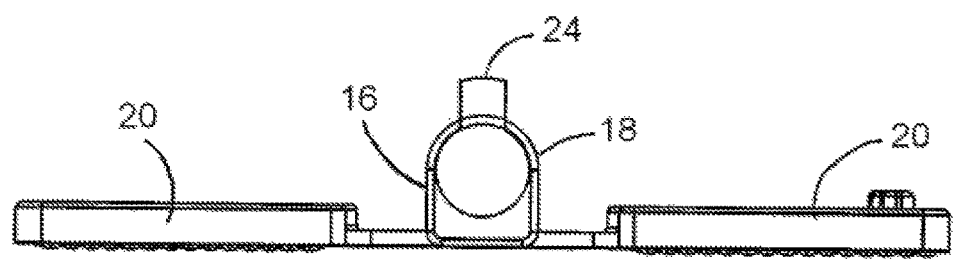
Figure 2C:
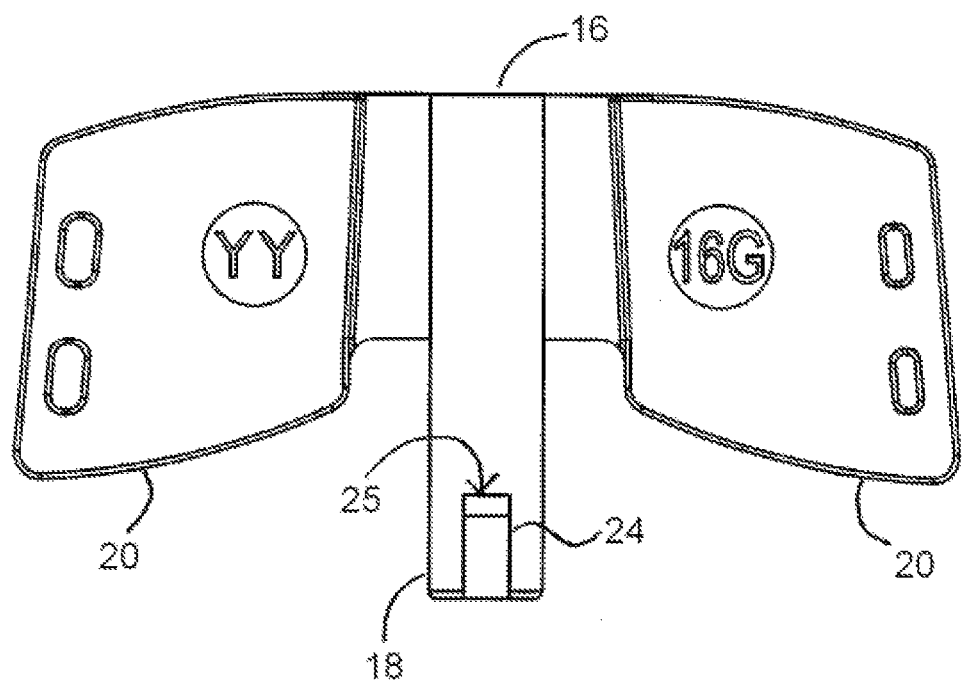
Figure 3A:
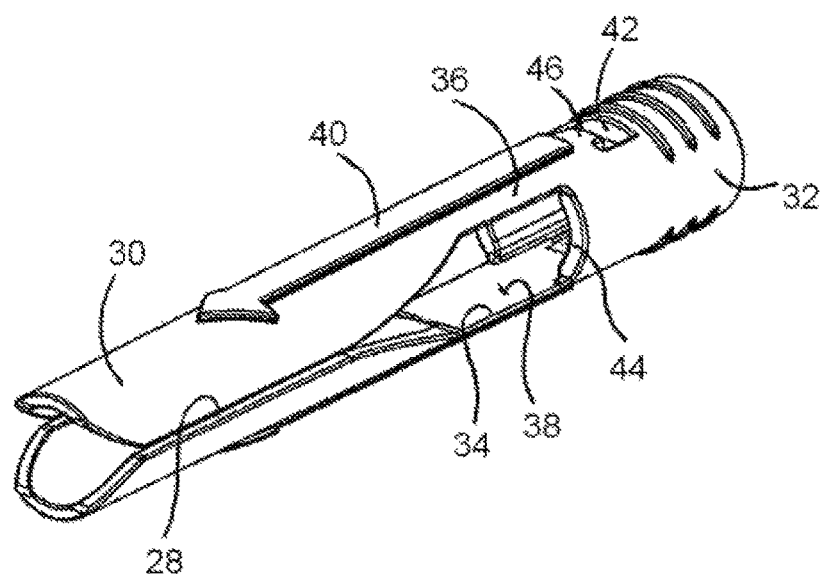
Figure 3B:
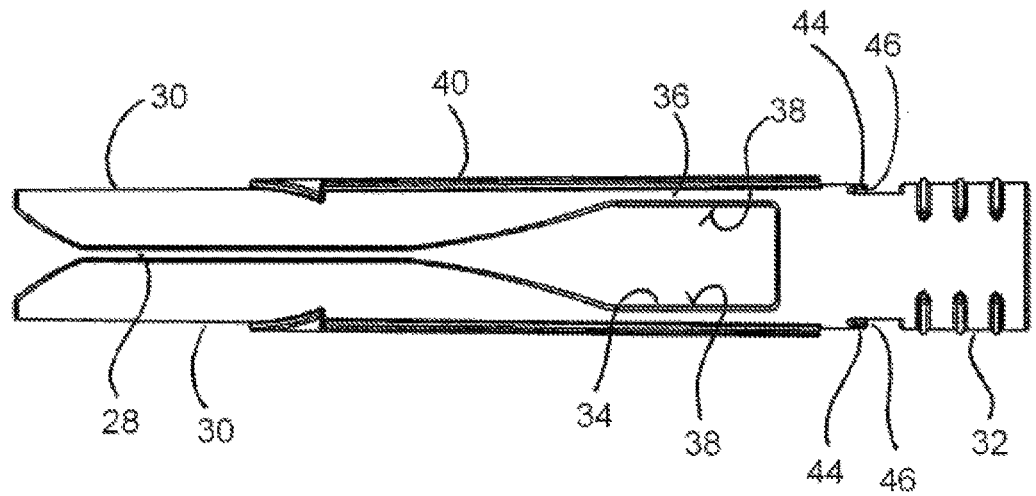
Figure 3:
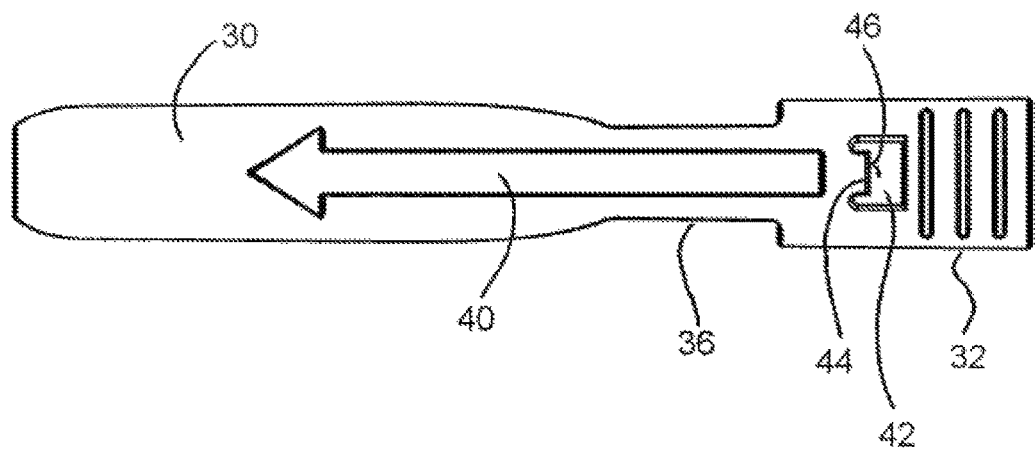

A preferred embodiment of the invention is described in the following description and in the accompanying drawings, wherein:

FIGS. 1(a), 1(b) and 1(c) show different views of a disposable medical device comprising a needle safety assembly of the invention, with a needle hub in a retracted position FIGS. 2(a), 2(b) and 2(c) show different views of a needle hub of the needle safety assembly shown in FIGS. 1(a), 1(b) and 1(c);

FIGS. 3(a), 3(b) and 3(c) show different views of a protective cover of the needle safety assembly shown in FIGS. 1(a), 1(b) and 1(c).

DETAILED DESCRIPTION OF THE INVENTION

FIGS. 1(a), 1(b) and 1(c) show a disposable medical device, for example a blood collection kit or a fistula needle kit, comprising a hypodermic needle 12 and a needle safety assembly 10 to prevent accidental contact of a medical professional or any other person with the sharp tip 14 of the needle 12 after use of the disposable medical device.

In this context, the end of the needle 12 having the sharp tip 14 is denoted the distal end, whereas the opposite end of the needle is denoted the proximal end. Likewise the orientation of parts of other structural elements facing towards the needle tip 14 will be referred to as distal, whereas the orientation of parts of these structural elements facing in the opposite direction will be referred to as proximal.

The needle 12 extends in an axial direction, thereby defining an axial direction for the needle safety assembly 10. A direction perpendicular to the axial direction is denoted as radial.

In the region of its proximal end the needle 12 is connected, for example glued, to a needle hub 16. The needle hub 16 is a so-called winged needle hub 16 having a tubular main body 18 and two wings 20 which extend in opposite radial directions from the main body 18. The wings 20 can either be formed integrally with the main body 18, or they can be separate elements that are attached to the main body 18.

One end of a PVC tube 22 is attached, for example glued, to a proximal end portion of the needle hub 16. The other end of the PVC tube 22 may, for example, be connected to a blood collection bag (not shown) or any other component to facilitate flow of fluid, such as medicine or blood, to or from a patient or donor. A clamp 23 is slidably arranged on the PVC tube 22 and can be used to close off the PVC tube 22.

As can be seen in FIGS. 1(a), 1(b) and 1(c), a locking protrusion 24 is arranged on a top side of the main body 18 of the needle hub 16 in a proximal region thereof. The locking protrusion 24 is integrally formed with the main body 18 and has a generally nose-like or ramp-like shape, with its radial dimension increasing towards the tip 14 of the needle 12. A distal face 25 of the locking protrusion 24 extends in a plane generally perpendicular to the axial direction, i.e. in a radial plane.

The position of the locking protrusion 24 is rotated by an angle of generally 90° about the needle axis with respect to the position of the wings 20, i.e. while the wings 20 extend in a first plane, e.g. a horizontal plane, the locking protrusion 24 extends in a second plane that is oriented generally perpendicular to the first plane, e.g. vertical.

As shown in FIGS. 1(a), 1(b) and 1(c), the needle safety assembly 10 further comprises a protective cover 26 which is slidably arranged on the PVC tube 22 and which can be pushed over the needle hub 16 and the needle 12 after the medical device has been used.

The protective cover 26, shown in more detail in FIGS. 1(a), 1(b) and 1(c), is of generally tubular shape, i.e. it has generally circular inner and outer cross-sections.

Two opposite axial slots 28 are formed in a wall of the protective cover 26 thereby defining first and second opposite part tubular axial sections 30 of the protective cover 26. The slots 28 extend from a distal end of the protective cover 26 towards a tubular base portion 32 of the protective cover 26 which is formed in a proximal end region of the protective cover 26.

The slots 28 are adapted to receive the wings 20 when the needle hub 16 moves into the protective cover 26 thereby ensuring a correct rotational position of the protective cover 26 relative to the needle hub 16.

The axial length of the slots 28 is greater than an axial distance between a proximal face of the wings 20 and the needle tip 14. In other words, the axial length of the slots 28 is selected such that the needle hub 16 and the needle 12 can be fully received inside the protective cover 26, in particular, with the needle tip 14 being inside the protective cover 26 and thereby effectively precluded from accidentally pricking someone.

Across a certain length, in the illustrated embodiment across almost half the axial length of the protective cover 26, the slots 28 have a minimum width which can be even smaller than the thickness of the wings 20.

Towards the distal end of the protective cover 26 the slots widen in order to facilitate the insertion of the wings 20 when the protective cover 26 is pushed over the needle hub 16. The slots 28 also widen towards the tubular base portion 32 and each comprise a significantly enlarged proximal region 34.

The enlarged proximal regions 34 of the slots 28 are defined by cut-outs in the tubular wall of the protective cover 26 and result in tapered proximal end portions 36 of the axial sections 80, which pass into the tubular base portion 32 and which have a thickness generally corresponding to the thickness of the tube wall. The proximal end portions 36 have opposite flat inner surfaces 38 which pass into corresponding flat surfaces inside the tubular base portion 32.

Elevated structures 40 are provided on the outer surfaces of the axial sections 30. More specifically, the elevated structures 40 are in the form of arrows indicating the direction in which the protective cover 26 is to be moved along the PVC tube 22 in order to cover the needle 14. Furthermore, the elevated structures 40 serve to strengthen the axial sections 30 in the region of their tapered proximal end portions 36.

The maximum inner diameter of the tubular protective cover 26 is smaller than the maximum radial dimension of the needle hub 16 in the region of the peak of the locking protrusion 24. Consequently, the axial sections 30 are spread apart when the needle hub 16 moves into the protective cover 26, with the tapered proximal end portions 36 providing a certain amount of flexibility and thereby facilitating the spreading apart of the axial sections 30 and thus making the movement of the needle hub 16 into the protective cover 26 easier.

It is to be noted that the transition from the minimum width regions of the slots 28 towards the enlarged proximal regions 34 of the slots 28 is continuous, more specifically follows a gentle curve. As such, this transition does not serve to lock the needle hub 16 in its retracted position inside the protective cover 26 and would not prevent undesirable re-emerging of the covered needle tip 14.

Instead, two locking openings 42 are provided in the tubular wall of the base portion 32 on opposite sides thereof. The position of the locking openings 42 is rotated by generally 90° about the needle axis with respect to the slots. As such at least one of the locking openings 42 is aligned with the locking protrusion 24 when the wings 20 move along the slots 28.

The axial position of the locking openings 42 is adapted such that the locking protrusion 24 engages one of the locking openings 42 when the needle 12 is fully received in the protective cover 26 and the wings 20 abut against the base portion 32.

An arrangement of two locking openings 42 simplifies a correct locking of the needle hub 16 inside the protective cover 26, since the protective cover 26 can be rotated by 180° about the PVC tube 22 and still be correctly locked with the needle hub 16. However, it is to he understood that a base portion 32 having only one locking opening 42 would work as well, only in this case the person handling the device would have to make sure that the single locking opening 42 is rotated to the side of the locking protrusion 24 when the protective cover 26 is pushed over the needle hub 16 in order to ensure a locking between the protective cover 26 and the needle hub 16.

In order to improve the desired locking function each locking opening 42 is provided with a locking tongue 44 which protrudes from a distal side of the locking opening 42 into the opening 42 and also into the interior of the base portion 32. More specifically, the locking tongues 44 have a ramp-like shape with its radial dimension increasing in a proximal direction and defining a proximal face 46 which extends in a plane generally perpendicular to the axial direction. In the locked state the distal face 25 of the locking protrusion 24 engages with the proximal face 46 of the locking tongue 44, thereby improving the locking effect and thus the safety of the needle safety assembly 10.

In order to make it easier for the locking protrusion 24 to move past the locking tongue 44 upon entering its locked position, the locking protrusion 24 may comprise or be made of a material having certain elastic properties, such as a plastic or silicon material. In fact, the entire needle hub 16 may be made of such a material.

In comparison, the protective cover 26 may be made of a rather stiff plastic material. Alternatively, the protective cover 26 may comprise or consist of a metal material.

The function of the needle safety assembly 10 is as follows:

In the initial state of the medical device, e.g. prior to use of the medical device, the needle hub 16 is outside the protective cover 26, with the protective cover 26 being moved along the PVC tube 22 away from the needle hub 16 as far as desired.

A medical professional holds the wings 20 attached to the needle hub 16 and punctures the skin of a patient with the needle 12 such that the needle 12 enters a vein of patient. As the needle 12 enters the vein blood rushes into the needle 12 and through the main body 18 of the needle hub 16 into the PVC tube 22. The blood is collected in a blood collection bag or a vacuum tube through a connection to the other end of the PVC tube 22. Alternatively, the device may be used to give fluids or medications to a patient.

After a required quantity of blood has been collected, the needle 12 is withdrawn from the vein and the protective cover 26 is pushed over the needle hub 16 with the wings 20 moving along the slots 28 until the locking protrusion 24 of the needle hub 16 engages with the locking opening 42 and the locking tongue 44 of the protective cover 26. The needle 12 is now fully received and locked inside the protective cover 26 and the blood collection set can be safely disposed of.

Although this invention has been disclosed in the context of certain preferred embodiments and examples, it will be understood by those skilled in the art that the present invention can be constructed and utilized in a plethora of different ways. It should be understood that many changes, modifications, variations and other uses and applications will become apparent to those persons skilled in this particular area of technology and to others after having been exposed to the present specification and accompanying drawings. Any and all such change, modifications, variations, and other uses and applications which do not depart from the spirit and scope of the present invention are therefore covered by and embraced within the present invention and the patent claims set forth herein-below.

REFERENCE NUMERALS 10 needle safety assembly
12 needle
14 needle tip
16 needle hub
18 main body
20 wing 22 PVC tube
23 clamp
24 locking protrusion
25 distal face
26 protective cover
28 slot
30 axial section
32 base portion
34 enlarged proximal region
36 end position
38 flat surface
40 elevated structure
42 locking opening
44 locking tongue
46 proximal face the invention claimed is:

1. A needle safety assembly comprising:
a needle;
a needle hub having wings extending outward on opposite sides of the needle hub and said needle hub having a locking projection extending from the needle hub; and
a protective cover for the needle having a locking opening on a top of the protective cover with said opening including a locking tongue extending towards a proximal end of the protective cover and adapted to engage with the locking projection when the needle hub is in the retracted position, said protective cover also having a pair of opposing axial slots on opposite sides of the protective cover, said slots extending to an opening on an end of the protective cover, said slots being closed at another end of the needle cover,
wherein the needle is attached to said needle hub which can be moved relative to the protective cover by sliding each one of said wings along perspective one of said axial slots from a position of use in which at least the tip of the needle is outside of the protective cover into a retracted position in which the needle is fully received in the protective cover and said locking projection of said needle hub engages with said locking opening of said protective cover to hold said needle hub within said protective cover,
wherein the protective cover is of generally tubular shape such that said opposing axial slots each extend from the opening provided at a distal end of the protective cover towards a tubular base portion of the protective cover, wherein the slots are adapted to receive the wings through the opening and move along the slots when the needle hub moves into the protective cover, and
wherein the protective cover can be completely removed from the needle hub by sliding the wings beyond the opening at the distal end.

2. A needle safety assembly in accordance with claim 1, wherein a position of the locking projection on the needle hub is rotated by an angle of generally 90° about the needle axis with respect to the position of the wings.

3. A needle safety assembly in accordance with claim 1, wherein the locking projection is formed integrally with the needle hub and/or the locking opening is formed integrally with the protective cover.

4. A needle safety assembly in accordance with claim 1, wherein the locking projection defines a surface facing the needle tip, wherein at least a portion of the surface extends in a plane generally perpendicular to the needle.

5. A needle safety assembly in accordance with claim 1, wherein the locking projection comprises a ramp-shaped protrusion protruding from the needle hub.

6. A needle safety assembly in accordance with claim 1, wherein locking projection has a generally nose-like or ramp-like shape, with its radial dimension increasing towards the tip of the needle.

7. A needle safety assembly in accordance with claim 1, wherein the locking projection is formed such that a radial dimension of the locking projection can be reduced against a restoring force.

8. A needle safety assembly in accordance with claim 1, wherein the locking projection comprises a material having elastic properties.

9. A needle safety assembly in accordance with claim 1, wherein the locking projection is arranged in the region of a proximal end of the needle hub.

10. A needle safety assembly in accordance with claim 1, wherein the locking opening is provided on the tubular base portion of the protective cover.

11. A needle safety assembly in accordance with claim 1, wherein the locking opening comprises an opening in the protective cover, which is adapted to receive the locking projection when the needle hub is in the retracted position.

12. A needle safety assembly in accordance with claim 1, wherein the locking tongue extends towards the interior of the protective cover and defines a proximal surface which extends in a generally radial plane.

13. A needle safety assembly comprising:
a needle;
a needle hub having wings extending outward on opposite sides of the needle hub and said needle hub having a ramp-shaped locking projection extending from the needle hub with one end of the projection being flush with a surface of the needle hub; and
a protective cover for the needle having a locking opening on a top of the protective cover with said opening including a locking tongue extending towards a proximal end of the protective cover and adapted to engage with the locking projection when the needle hub is in the retracted position, said protective cover also having a pair of opposing axial slots on opposite sides of the protective cover, said slots extending to an opening on an end of the protective cover, said slots being closed at another end of the needle cover,
wherein the needle is attached to said needle hub which can be moved relative to the protective cover by sliding each one of said wings along perspective one of said axial slots from a position of use in which at least the tip of the needle is outside of the protective cover into a retracted position in which the needle is fully received in the protective cover and said locking projection of said needle hub engages with said locking opening of said protective cover to hold said needle hub within said protective cover,
wherein the protective cover is of generally tubular shape and such that said opposing axial slots each extend from the opening provided at a distal end of the protective cover towards a tubular base portion of the protective cover, wherein the slots are adapted to receive the wings through the opening and move along the slots when the needle hub moves into the protective cover, and
wherein the protective cover can be completely removed from the needle hub by sliding the wings beyond the opening at the distal end,
wherein the locking tongue extends towards the interior of the protective cover and defines a proximal surface which extends in a generally radial plane.

14. A needle safety assembly comprising:

a needle;

a needle hub having wings extending outward on opposite sides of the needle hub and said needle hub having a ramp-shaped locking projection extending from the needle hub; and a protective cover for the needle having a locking opening on a top of the protective cover with said opening including a locking tongue extending towards a proximal end of the protective cover and adapted to engage with the locking projection when the needle hub is in the retracted position, said protective cover also having a pair of opposing axial slots on opposite sides of the protective cover, said slots extending to an opening on an end of the protective cover, said slots being closed at another end of the needle cover, wherein the needle is attached to said needle hub which can be moved relative to the protective cover by sliding each one of said wings along perspective one of said axial slots from a position of use in which at least the tip of the needle is outside of the protective cover into a retracted position in which the needle is fully received in the protective cover and said locking projection of said needle hub engages with said locking opening of said protective cover to hold said needle hub within said protective cover, wherein the protective cover is of generally tubular shape a such that said opposing axial slots each extend from the opening provided at a distal end of the protective cover towards a tubular base portion of the protective cover, wherein the slots are adapted to receive the wings through the opening and move along the slots when the needle hub moves into the protective cover, and wherein the protective cover can be completely removed from the needle hub by sliding the wings beyond the opening at the distal end.

\* \* \* \* \*